United States Patent [19]
Park et al.

[11] Patent Number: 5,929,754
[45] Date of Patent: Jul. 27, 1999

[54] HIGH-SENSITIVITY CAPACITIVE OIL DETERIORATION AND LEVEL SENSOR

[75] Inventors: Kyong M. Park, Thousand Oaks; Nhan Nguyen, Simi Valley, both of Calif.

[73] Assignee: Kavlico Corporation, Moorpark, Calif.

[21] Appl. No.: 08/984,584

[22] Filed: Dec. 3, 1997

[51] Int. Cl.$^6$ ................................................. B60Q 1/00
[52] U.S. Cl. ........................ 340/439; 340/450.3; 340/618; 340/631; 324/663; 73/53.05; 73/54.02; 73/54.01; 73/304 C
[58] Field of Search ............................... 340/439, 450.3, 340/438, 450, 612, 620, 618, 603, 631; 324/663, 71.1, 658; 73/304 C, 53.05, 54.01, 54.02, 724, 718, 61.43

[56] References Cited

U.S. PATENT DOCUMENTS

| | | | |
|---|---|---|---|
| 2,462,715 | 2/1949 | Booth ........................................ | 340/631 |
| 2,807,956 | 10/1957 | Doble ........................................... | 73/73 |
| 3,046,537 | 7/1962 | Dow ........................................... | 340/234 |
| 3,067,385 | 12/1962 | Rykoskey ................................... | 324/61 |
| 3,196,667 | 7/1965 | Alquist et al. .............................. | 73/53 |
| 3,424,977 | 1/1969 | Krobath ....................................... | 324/61 |
| 3,522,530 | 8/1970 | Muller ......................................... | 324/65 |
| 3,523,245 | 8/1970 | Love et al. .................................. | 324/61 |
| 3,622,875 | 11/1971 | Ichijo ....................................... | 324/61 R |
| 3,675,121 | 7/1972 | Thompson ............................... | 324/61 R |
| 3,746,974 | 7/1973 | Stoakes et al. ......................... | 324/61 R |
| 3,816,811 | 6/1974 | Cmelik ................................... | 324/61 R |
| 3,876,916 | 4/1975 | Stoakes ................................ | 317/249 R |
| 3,946,494 | 3/1976 | Wells ......................................... | 33/366 |
| 3,992,951 | 11/1976 | Erspamer et al. ........................ | 73/497 |
| 4,048,844 | 9/1977 | Dunikowski et al. ................... | 73/32 R |
| 4,064,455 | 12/1977 | Hopkins et al. ....................... | 324/61 R |
| 4,227,419 | 10/1980 | Park ........................................ | 73/724 |
| 4,345,202 | 8/1982 | Nagy et al. ......................... | 324/58.5 B |
| 4,398,426 | 8/1983 | Park et al. ............................... | 73/724 |
| 4,409,832 | 10/1983 | Konjedic et al. ........................ | 73/292 |
| 4,422,243 | 12/1983 | Brunson et al. .......................... | 33/366 |
| 4,468,611 | 8/1984 | Tward .................................... | 324/61 R |
| 4,470,300 | 9/1984 | Kobayashi ................................ | 73/304 |
| 4,521,973 | 6/1985 | Wiklund et al. .......................... | 33/366 |
| 4,559,493 | 12/1985 | Goldberg et al. ...................... | 324/61 R |
| 4,617,607 | 10/1986 | Park et al. ................................ | 361/283 |
| 4,641,434 | 2/1987 | Engler ........................................ | 33/366 |
| 4,644,662 | 2/1987 | Anderson et al. ......................... | 33/366 |
| 4,646,070 | 2/1987 | Yasuhara et al. ......................... | 340/603 |
| 4,706,193 | 11/1987 | Imajo et al. ............................. | 364/424 |
| 4,707,927 | 11/1987 | Hiyama ...................................... | 33/366 |
| 4,733,556 | 3/1988 | Meitzler et al. ............................. | 73/64 |
| 4,806,847 | 2/1989 | Atherton et al. ........................ | 324/61 P |
| 4,811,491 | 3/1989 | Phillips et al. ............................ | 33/366 |
| 4,846,954 | 7/1989 | Ryan et al. ................................ | 33/366 |
| 4,899,102 | 2/1990 | Hendrick et al. ........................ | 324/663 |
| 4,912,662 | 3/1990 | Butler et al. ............................. | 364/559 |
| 4,924,702 | 5/1990 | Park ........................................... | 73/304 |
| 4,945,863 | 8/1990 | Schmitz et al. .......................... | 123/1 A |
| 4,981,039 | 1/1991 | Hayashi et al. ............................ | 73/292 |

(List continued on next page.)

FOREIGN PATENT DOCUMENTS 0080632  6/1983  European Pat. Off. ........ G01N 27/22

OTHER PUBLICATIONS

Dean R. Harrison and John Dimeff, "Transducers," *Rev. Sci. Instrum.* vol. 44, No. 10, Oct., 1973, pp. 1468–1472.

*Primary Examiner*—Jeffery A. Hofsass
*Assistant Examiner*—Sihong Huang
*Attorney, Agent, or Firm*—Oppenheimer Wolff & Donnelly LLP

[57] ABSTRACT

A high-sensitivity capacitive oil deterioration and level sensor includes a conductive housing member with an inner surface defining a ground electrode and conductive inner member with an outer surface defining a measuring electrode. The housing member is adapted to provide a fluidic connection between an oil container and a gap between the ground electrode and the measuring electrode. The sensor also includes electronics adapted to employ this capacitor geometry to generate signals indicative of a degree of deterioration and a level of the oil within the gap.

22 Claims, 6 Drawing Sheets

U.S. PATENT DOCUMENTS

| | | | |
|---|---|---|---|
| 5,060,108 | 10/1991 | Baker et al. | 361/283 |
| 5,083,383 | 1/1992 | Heger | 33/366 |
| 5,103,184 | 4/1992 | Kapsokavathis et al. | 324/672 |
| 5,125,265 | 6/1992 | O'Connell et al. | 73/61.41 |
| 5,170,567 | 12/1992 | Davis et al. | 33/366 |
| 5,179,926 | 1/1993 | Ament | 123/494 |
| 5,182,523 | 1/1993 | Ertel et al. | 324/663 |
| 5,205,151 | 4/1993 | Shimamura et al. | 73/1 R |
| 5,233,875 | 8/1993 | Obermeier et al. | 73/718 |
| 5,237,753 | 8/1993 | Carlson et al. | 33/366 |
| 5,261,270 | 11/1993 | Gonze et al. | 73/61.43 |
| 5,261,279 | 11/1993 | Wolf et al. | 73/517 R |
| 5,262,732 | 11/1993 | Dickert et al. | 324/672 |
| 5,274,335 | 12/1993 | Wang et al. | 324/689 |
| 5,281,922 | 1/1994 | Lofgren et al. | 324/684 |
| 5,283,711 | 2/1994 | Schmitz | 361/286 |
| 5,284,056 | 2/1994 | Randolph et al. | 73/440 |
| 5,299,456 | 4/1994 | Steiner | 73/308 |
| 5,309,110 | 5/1994 | O'Neill et al. | 324/674 |
| 5,313,168 | 5/1994 | Ogawa | 324/663 |
| 5,329,819 | 7/1994 | Park et al. | 73/724 |
| 5,331,845 | 7/1994 | Bals et al. | 73/61.43 |
| 5,335,190 | 8/1994 | Nagle et al. | 364/571.01 |
| 5,337,017 | 8/1994 | Ogawa | 324/682 |
| 5,367,264 | 11/1994 | Brabetz | 324/674 |
| 5,418,465 | 5/1995 | Seipler et al. | 324/663 |
| 5,435,170 | 7/1995 | Voelker et al. | 73/53.05 |
| 5,469,632 | 11/1995 | Boenning | 33/366 |
| 5,479,716 | 1/1996 | Murphy | 33/366 |
| 5,488,311 | 1/1996 | Kamioka et al. | 324/674 |
| 5,540,086 | 7/1996 | Park et al. | 73/53.05 |
| 5,604,441 | 2/1997 | Freese et al. | 324/663 |
| 5,656,780 | 8/1997 | Park | 73/724 |

HIGH-SENSITIVITY CAPACITIVE OIL DETERIORATION AND LEVEL SENSOR

BACKGROUND OF THE INVENTION

1. Field of the Invention

The present invention relates to a multi-functional sensor and, more particularly, pertains to a high-sensitivity capacitive oil deterioration and level sensor adapted to generate signals indicative of oil deterioration and oil level.

2. Description of the Related Art

One of the most important factors that contributes to the efficiency and durability of internal combustion engines is lubrication. As engine oil "breaks down" it is less effective in protecting an engine from damage caused by friction between engine parts. More specifically, the normal life span of motor oils is limited by thermal breakdown, additive depletion and carbon particulates that result from the combustion process.

The deterioration of engine oil is marked by a decrease in the viscosity of the oil. The dielectric constant of engine oil provides an indication of the oil's deterioration or lack thereof. The dielectric constant of motor oil is typically between 1.6 and 3.2 depending upon its brand and age. For example, the dielectric constant of a particular brand of motor oil may increase from 2.19 to 3.2 after 400 hours of use in a particular internal combustion engine under certain operating conditions. Thus, it is desirable to have a means for indicating when engine oil has deteriorated to the point where it should be changed.

Premature lubrication failure can also result from the presence of contaminants in the engine oil such as coolant (glycol ethylene), fuel or water. The presence of these contaminants in motor oil is often indicative of a mechanical failure such as a damaged head gasket or a broken piston ring. Water and engine coolant have dielectric constants of approximately 87.5 and 37.0, respectively. The introduction of such contaminants into the engine oil significantly increases the dielectric constant of some of the fluid which circulates through the engine for the purpose of lubrication. Thus, it is also desirable to have a means for detecting the presence of these substances in engine oil.

Lubrication is also critical in applications which do not involve combustion but where oil is still monitored for degradation, e.g., compressors, pumps, and gearboxes. Thus, it is also desirable to have a means for detecting lubricant deterioration or the presence of foreign elements in lubricating oil.

U.S. Pat. No. 5,540,086 to Park et al. discloses an oil deterioration sensor adapted to monitor changes in the dielectric constant of oil. The disclosed oil deterioration sensor includes a capacitor geometry consisting of two flat, circular plates separated by a fixed gap. One of the plates is a ceramic disk upon which gold has been deposited to form an electrode. The other capacitor terminal, the ground electrode, consists of a portion of the sensor housing. This geometry works very well in most applications. However, this is not so in some cases, such as gearboxes, in which the change in dielectric constant is very small resulting in excessive gain requirements on the amplification circuit. Thus, it is also desirable to have a means for detecting small changes in the dielectric constant of oil.

Today's luxury automobiles rely heavily upon control systems which receive input signals from a wide variety of sensing devices. To ensure proper functioning of these control systems, a large number of highly dependable and accurate electronic transducers are needed to provide the aforementioned input signals. However, the implementation of too many transducers has proven to be uneconomical for automobile manufacturers. Thus, a single sensor including a plurality of transducers and their associated signal conditioning electronics is also desirable.

The dielectric constant of oil is also influenced by the temperature of the oil and by the specific formulation of a given brand of oil. Thus, it is also desirable to provide a multi-functional sensor with a means for compensating for changes in the dielectric constant of oil resulting from these factors.

Accordingly, an object of the present invention is to provide a high-sensitivity capacitive oil deterioration and level sensor which is adapted to detect small changes in the dielectric constant of oil.

Another object is to provide a high-sensitivity capacitive oil deterioration and level sensor which employs a cylindrical capacitor electrode geometry to generate signals indicative of a degree of oil deterioration and a level of the oil within the sensor.

Another object is to provide a high-sensitivity capacitive oil deterioration and level sensor with a capacitor geometry which eliminates the need for costly gold plating of electrodes.

Another object is to provide a high-sensitivity capacitive oil deterioration and level sensor including a reference capacitor which partially compensates for the difference in dielectric constant of different oil brands and for any geometric changes caused by thermal expansion of materials comprising the sensor, and to cancel stray capacitances arising in the wiring of the electrodes to circuitry within the sensor.

SUMMARY OF THE INVENTION

In accordance with a specific illustrative embodiment of the present invention, a high-sensitivity capacitive oil deterioration and level sensor includes a conductive housing member, a conductive inner member, an electrical connector, a reference capacitor and electronics. The conductive housing member includes a cylindrical portion with an inner surface defining a ground electrode. The housing member includes a threaded outer surface adapted to be threaded into an oil container of an internal combustion engine. The housing member is formed with at least one port sized to allow oil within the oil container to enter into the cylindrical portion of the housing member. The conductive inner member includes a cylindrical portion with an outer surface defining a measuring electrode. The inner member is secured within the housing member such that the ground electrode and the measuring electrode define an oil deterioration and level sensor capacitor. The electrical connector is adapted to provide an electrical interface to a processor. The reference capacitor is positioned within the housing member. The electronics are positioned within the housing member. The electronics are electrically connected to the oil deterioration and level sensor capacitor, the reference capacitor, and the electrical connector. The electronics are adapted to generate an oil deterioration output signal and an oil level output signal employing the oil deterioration and level sensor capacitor and the reference capacitor and to provide the signals to the electrical connector.

In another aspect of the present invention, the high-sensitivity capacitive oil deterioration and level sensor includes a conductive housing member, a conductive inner member, an upper spacer and electronics. The conductive housing member includes a cylindrical portion with an inner surface defining a ground electrode. The housing member includes a threaded outer surface adapted to be threaded into an oil container of an internal combustion engine. The housing member is formed with at least one port sized to allow oil within the oil container to enter into the cylindrical portion of the housing member. The conductive inner member includes a cylindrical portion with an outer surface defining a measuring electrode. The inner member is sized to be fitted within the housing member such that the ground electrode and the measuring electrode define an oil deterioration and level sensor capacitor. The upper spacer is positioned between the housing member and the inner member. The upper spacer is sized to maintain a substantially concentric relationship between the ground electrode and the measuring electrode. The electronics are positioned within the housing member. The electronics are electrically connected to the oil deterioration and level sensor capacitor and adapted to provide an oil deterioration output signal and an oil level output signal employing the oil deterioration and level sensor capacitor.

In another aspect of the present invention, the high-sensitivity capacitive oil deterioration and level sensor includes a conductive housing member, a conductive inner member and electronics. The conductive housing member has an inner surface defining a ground electrode. The conductive inner member has an outer surface defining a measuring electrode. The inner member is secured within the housing member such that a gap is maintained between the ground electrode and the measuring electrode, with the electrodes defining in oil deterioration and level sensor capacitor. The housing member is attached to an oil container of an internal combustion engine and adapted to provide a fluidic connection between the oil container and the gap permitting oil within the oil container to flow into the gap. The electronics are positioned within the housing member. The electronics are electronically connected to the oil deterioration and level sensor capacitor and adapted to employ the capacitor to generate signals indicative of a degree of deterioration and a level of the oil within the gap.

In another aspect of the present invention, the high-sensitivity capacitive oil deterioration and level sensor includes a conductive tube member, a conductive measuring tube secured within the tube member, and a conductive electrode secured within the tube member below the measuring tube. The tube member and the measuring tube define a measuring electrode for oil level detection. The tube member and the electrode define a reference electrode for oil level detection and a measuring electrode for oil deterioration sensing. The tube member, measuring tube, and electrode are electrically connected to electronics which are adapted to generate signals indicative of a degree of deterioration and a level of oil within the sensor.

In a broader aspect of the present invention, the high-sensitivity capacitive oil deterioration and level sensor includes at least three electrodes defining a plurality of capacitors which are electrically connected to electronics for generating signals indicative of a degree of deterioration and a level of oil within the sensor, one of said electrodes being employed as an electrode in at least two of the capacitors.

DESCRIPTION OF THE DRAWINGS

Other objects, features and advantages of the invention will become readily apparent upon reference to the following detailed description when considered in conjunction with the accompanying drawings, in which like reference numerals designate like parts throughout the figures thereof, and wherein.

DETAILED DESCRIPTION OF THE PREFERRED EMBODIMENTS

Figures 1, 3:
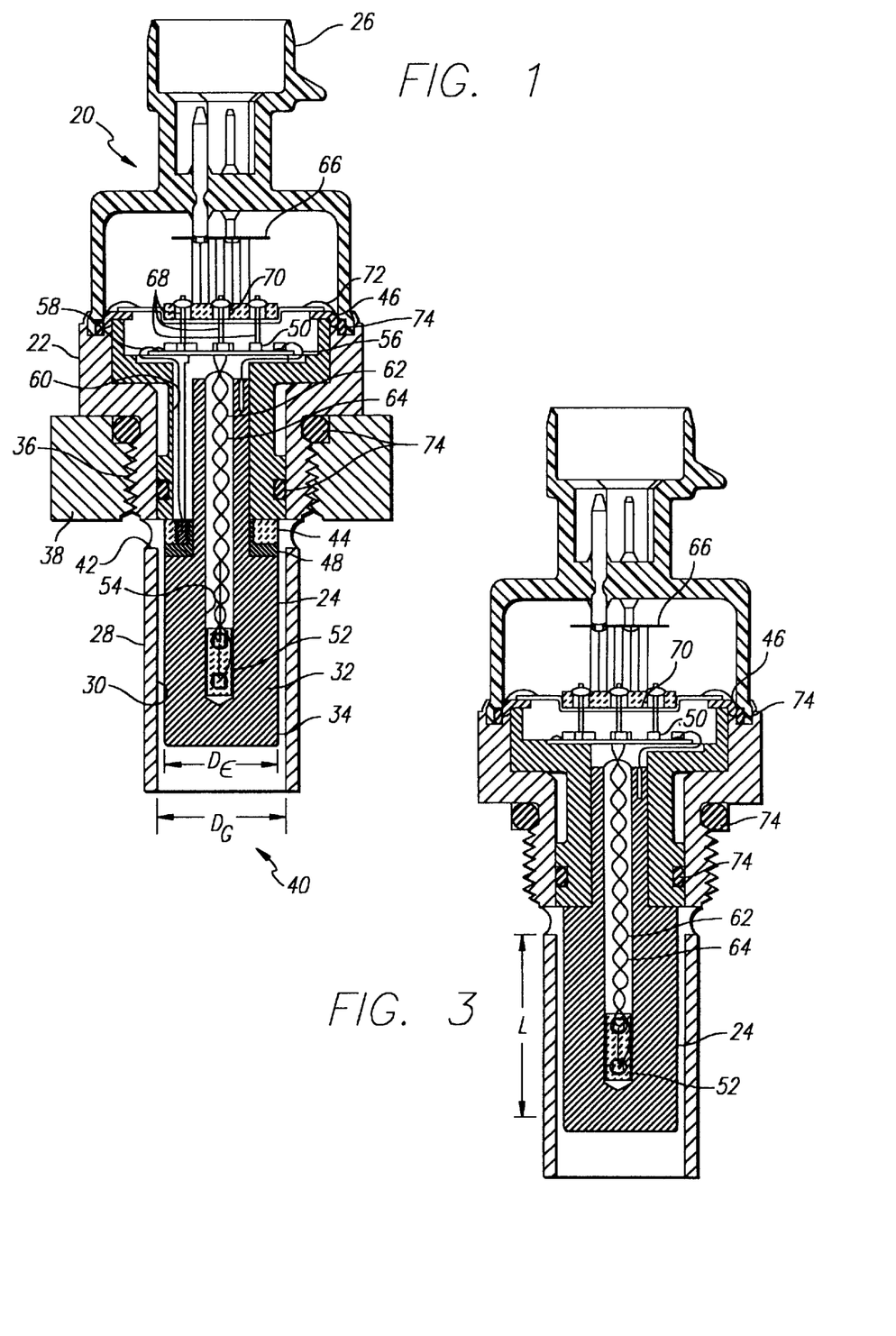
FIG. 1 is a cross-sectional side view of an exemplary preferred embodiment of a high-sensitivity capacitive oil deterioration and level sensor according to the present invention.
FIG. 3 is a cross-sectional side view of an alternative exemplary preferred embodiment of a high-sensitivity capacitive oil deterioration and level sensor according to the present invention.

FIG. 1 is a cross-sectional side view of a preferred exemplary embodiment of a high-sensitivity capacitive oil deterioration and level sensor 20 according to the present invention. The sensor 20 includes a conductive housing member 22, a conductive inner member 24, and an electrical connector 26 which are interfitted as shown.

The housing member 22 includes a cylindrical portion 28 with an inner surface 30 which defines a ground electrode. The inner member 24 includes a cylindrical portion 32 with an outer surface 34 which defines a measuring electrode. The inner member 24 is secured within the housing member 22 such that the ground electrode 30 and the measuring electrode 34 define an oil deterioration and level sensor capacitor ($C_e$).

The housing member 22 also includes a threaded outer surface 36 which, in a preferred embodiment, is adapted to be threaded into an oil container 38 of an internal combustion engine. The scope of the present invention additionally contemplates applications which do not involve combustion but where oil is still monitored for degradation, e.g., compressors, pumps, and gearboxes.

Figures 2, 7:
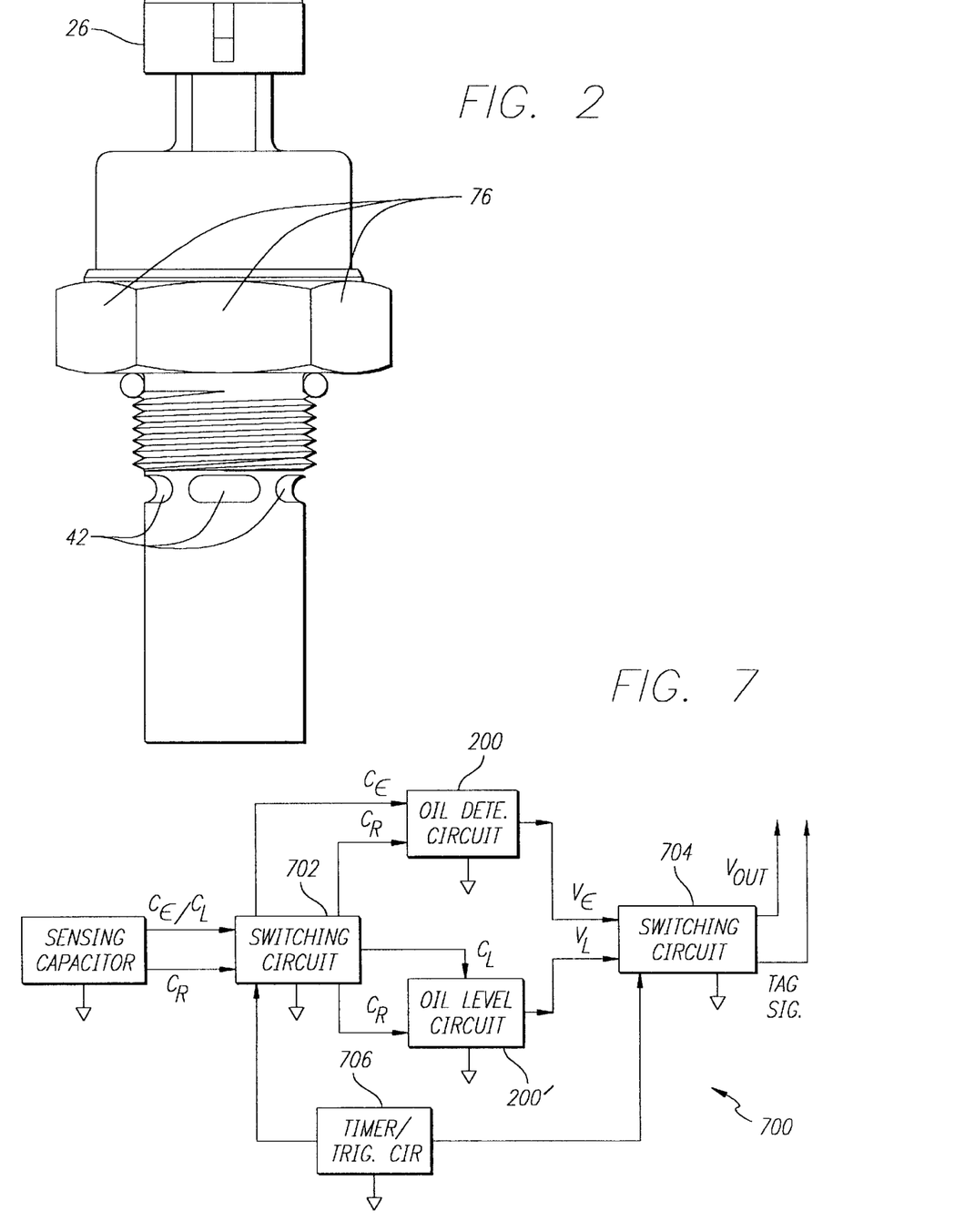
FIG. 2 is a side view of the high-sensitivity capacitive oil deterioration and level sensor of FIG. 1.
FIG. 7 is a functional block diagram showing circuitry for providing an oil deterioration output signal and an oil level output signal.

The housing member 22 is formed with at least one port sized to allow oil within the oil container 38 to enter into the cylindrical portion 28 of the housing member 22. In the illustrated preferred embodiment, the at least one port comprises an open end 40 of the cylindrical portion 28 and a plurality of drain holes 42 which are best illustrated in FIG. 2.

Referring to FIG. 1, the sensor 20 additionally includes a reference capacitor ($C_{ref}$). In the illustrated preferred embodiment, the reference capacitor ($C_{ref}$) comprises an oil deterioration and level reference capacitor ($C_r$) and an external fixed reference capacitor ($C_{fixed}$); i.e., $C_{ref}=C_r+C_{fixed}$. The oil deterioration and level reference capacitor ($C_r$) is formed by the ground electrode 30 and a reference electrode 44 positioned within the housing member 22. The reference electrode 44 is positioned in between and supported by an upper spacer 46 and a lower spacer 48 as shown in FIG. 1.

The upper spacer 46 is positioned between the housing member 22 and the inner member 24 such that the measuring electrode 34 is concentrically positioned relative to the ground electrode 30. To this end, the ground electrode 30 and the measuring electrode 34 are preferably cylindrical in shape. As may be readily appreciated, the subject matter of the present invention contemplates capacitor geometries other than the aforedescribed cylindrical geometry.

Further with regard to the oil deterioration and level sensor capacitor ($C_\epsilon$), the capacitance of the cylindrical capacitor is given by:

$$C_\epsilon = 2\pi \epsilon L / \log(D_e/D_G),$$

where:

$\epsilon$ is the dielectric constant of the oil within the gap between the inner surface 30 and the outer surface 34;

L is the length of the cylinders (see FIG. 3);

$D_e$ is the outside diameter of the cylindrical portion 32 of the inner member 24; and $D_G$ is the inside diameter of the cylindrical portion 28 of the housing member 22.

Electronics positioned within the housing member 22 include the oil deterioration and level sensor capacitor ($C_\epsilon$), the reference capacitor ($C_{ref}$), and additional circuit elements which are preferably provided in an integrated circuit 50 (e.g., a hybrid integrated circuit). The electronics also include a temperature variable element 52 positioned within the housing member 22 and thermally connected to the oil. The temperature variable element preferably comprises a conventional temperature sensitive resistor 52 which is positioned within a channel 54 formed through the inner member 24 as shown in FIG. 1.

The hybrid circuit 50 is positioned within the housing member 22 and supported by the upper spacer 46. A plurality of conductive leads connect the electronics within the hybrid circuit 50 to the oil deterioration and level sensor capacitor ($C_\epsilon$), the reference capacitor ($C_{ref}$) and the temperature sensitive resistor 52. A lead 56 electrically connects the hybrid circuit 50 to the inner member 24. A lead 58 is routed through a conduit 60 in the upper spacer 46 to electrically connect the hybrid circuit 50 to the reference electrode 44. Leads 62, 64 provide an electrical connection between the hybrid circuit 50 and the temperature sensitive resistor 52.

The electrical connector 26 includes conductive terminals to provide power to the electronics and easy access to the output signals generated by the electronics. The terminals are electrically connected to the hybrid circuit 50 via a flexible strip 66, which includes wiring elements, and leads 68. A feed-through plate assembly 70 supports the flexible strip 66 and the leads 68. The feed-through plate assembly 70, in turn, is secured to the housing member 22 by, for example, solder joints 72. The sensor 20 additionally includes a plurality of conventional o-ring gaskets 74 configured as shown.

As shown in FIG. 2, the preferred sensor 20 includes a hexagonal exterior surface 76 which permits a mechanic, vehicle owner, etc. to thread the sensor 20 into or out of the oil container 38 with a conventional wrench. Other mechanical structures facilitating the mounting and insertion of the sensor 20 into the oil pan of an engine may also be employed.

As discussed above, the electronics are electrically connected to the oil deterioration and level sensor capacitor ($C_\epsilon$). As discussed below in greater detail, the electronics are adapted to employ the capacitor ($C_\epsilon$) to generate signals indicative of a degree of deterioration and a level of the oil within the gap.

Figure 4:
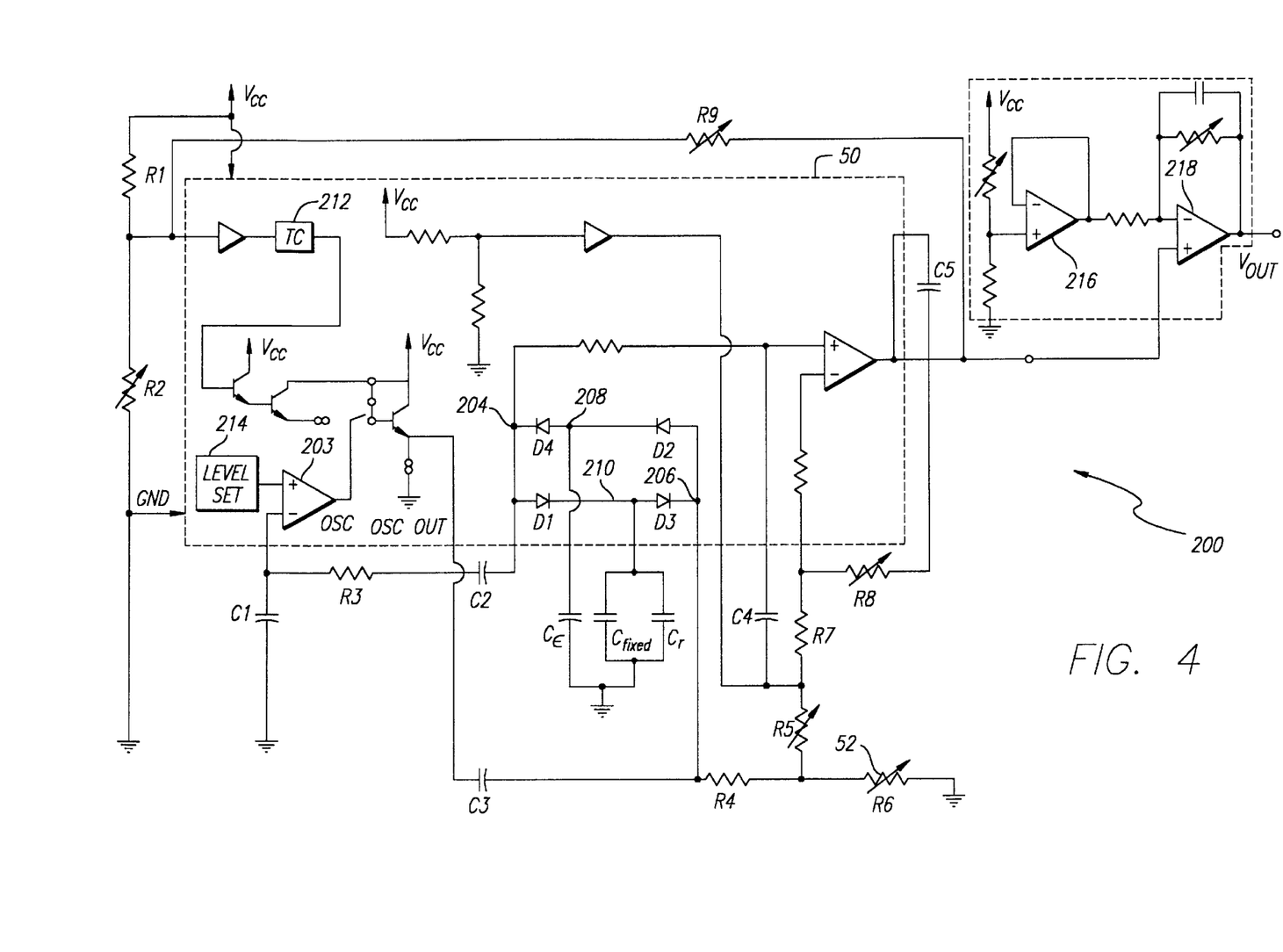
FIG. 4 is an electrical schematic of circuitry within the high-sensitivity capacitive oil deterioration and level sensor for generating an indication of oil deterioration or oil level.

FIG. 4 is an electrical schematic of circuitry 200 within the sensor 20 for generating an indication of engine oil dielectric constant and, more particularly, the oil deterioration output signal designated as ($V_{OUT}$). For the purpose of simplification, the operating supply voltage ($V_{cc}$) and a ground (GND) are generally shown as being provided to the hybrid 50. As may be readily appreciated, the dashed-line boundary of the hybrid 50 may be adjusted as circuit elements are either added to or relocated externally from the hybrid 50.

Generally, a capacitive transducer must be excited by an alternating current (AC) carrier voltage. Demodulating electronics are also needed to generate a direct current (DC) output. Accordingly, the circuitry 200 includes a diode-quad circuit 202 which is excited by a AC carrier voltage provided by an oscillator (OSC) 203. The diode-quad circuit 202 further includes diodes D1, D2, D3 and D4 arranged to form nodes 204, 206, 208, 210. More specifically, the anode of D1 and the cathode of D4 are electrically connected at the node 204, the anode of D2 and the cathode of D3 are electrically connected at the node 206, the cathode of D2 and the anode of D4 are electrically connected at the node 208, and the cathode of D1 and the anode of D3 are electrically connected at the node 210.

The oil deterioration output signal ($V_{OUT}$) is generated by the circuitry 200 and is described by the following formula:

$$V_{OUT} (C_\epsilon - C_{ref})/(C_\epsilon + C_{ref})$$

The oil deterioration and level sensor capacitor ($C_\epsilon$) is electrically connected across the node 208 and GND. The reference capacitor ($C_{ref}$), which comprises the oil deterioration and level reference capacitor ($C_r$) and the external fixed reference capacitor ($C_{fixed}$) configured in parallel, is electrically connected across the node 210 and GND. Since the capacitors $C_\epsilon$, $C_r$ and $C_{fixed}$ are not included within the hybrid 50, they are shown outside the dashed-line outlining the hybrid 50.

The oil deterioration and level reference capacitor ($C_r$) is used to minimize the differences between the respective dielectric breakdown characteristics of various motor oil formulations. The capacitance of $C_{fixed}$ is chosen such that $C_\epsilon$ is approximately equal to $C_{ref}$ when fresh motor oil is introduced into the gap.

After the motor oil begins to break down, the respective capacitances of $C_\epsilon$ and $C_{ref}$ both change, with $C_\epsilon$ being more sensitive to changes in the dielectric constant of the motor oil than $C_{ref}$.

As shown in FIG. 4, the preferred circuitry 200 also includes a temperature compensation element 212 and a level set 214 for the oscillator 203. These additional elements are conventional with the temperature compensation element 212 regulating the output of the oscillator 203 under changing environmental conditions.

Further with regard to temperature compensation, the temperature sensitive resistor 52 is designated as R6 and adjusts $V_{OUT}$ to compensate for changes in $V_{OUT}$ caused by changes in the temperature of the engine oil.

The preferred circuitry 200 further includes an external offset circuit 216 and an external gain circuit 218 which receive and adjust the output of the diode-quad circuit 202 as required to provide $V_{OUT}$. The aforedescribed signal conditioning may also be provided by alternative embodiments of the circuitry 200. For example, an alternative embodiment of the circuitry may include diode-quad circuits such as those described in "Transducers" by Dean R. Harrison and John Dimeff, Rev. Sci. Instrum., Vol. 44, No. 10, October 1973 which is herein incorporated by reference.

Other circuits such as those disclosed in U.S. Pat. Nos. 4,227,419 and 4,398,426, assigned to the assignee of this invention, may also be employed.

Figure 5:
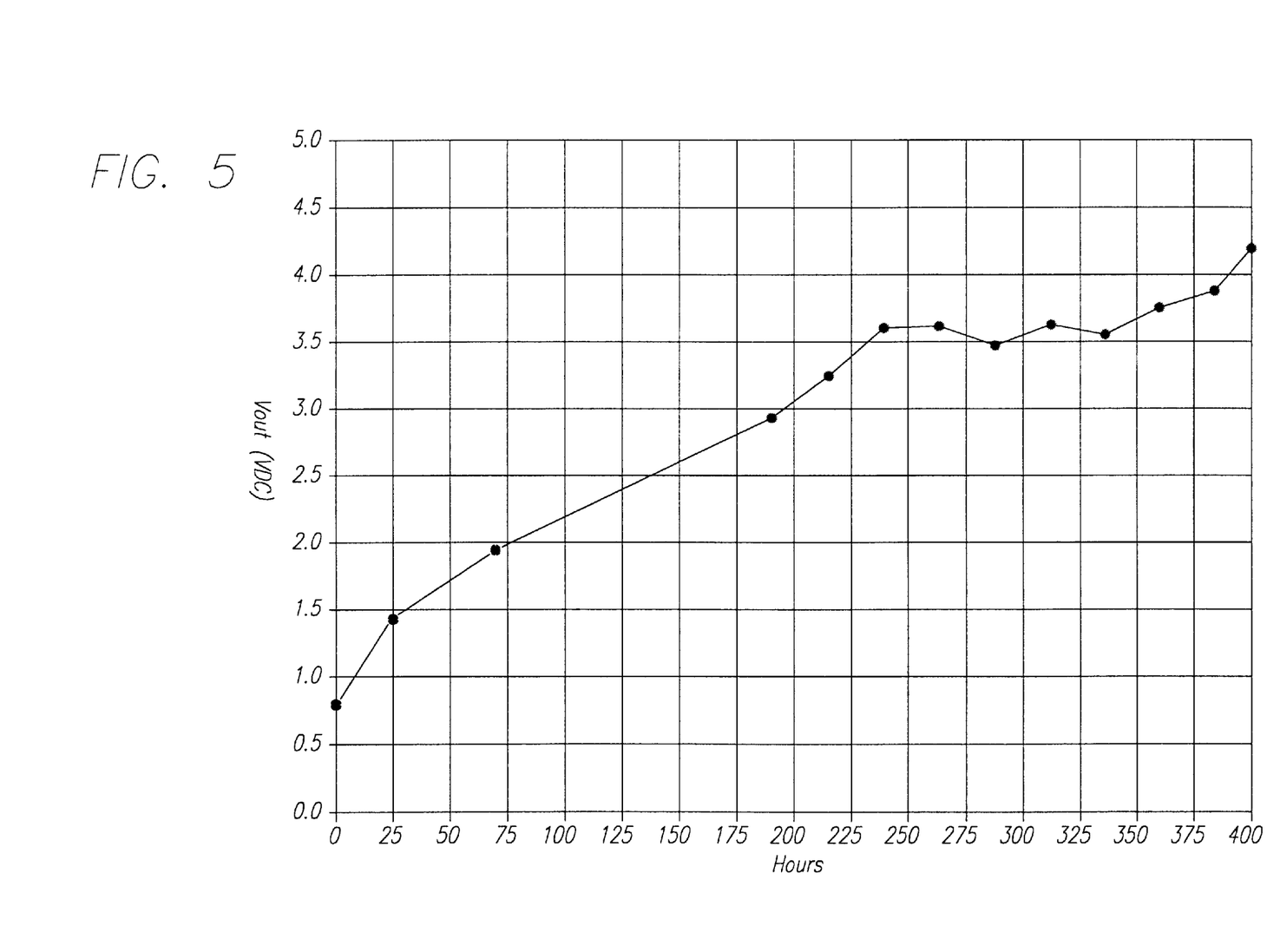
FIG. 5 is a plot of an output voltage (VDC) of the sensor at room temperature over time (hours) showing deterioration of the engine oil under test over time.

FIG. 5 is a plot of the sensor's output indication voltage (VDC) at room temperature over time (hours) of operation of an internal combustion engine. Since the dielectric constant of motor oil increases as the oil breaks down, the plot of FIG. 5 demonstrates that $V_{OUT}$ is proportional to $(C_\epsilon - C_{ref})/(C_\epsilon + C_{ref})$. As discussed above, the capacitance of $C_{fixed}$ is chosen such that $C_\epsilon$ is approximately equal to $C_{ref}$ when fresh motor oil is introduced into the gap so that the engine oil deterioration indication signal ($V_{OUT}$) initially generated by the circuitry 200 measures close to 0.0 VDC. As the motor continues to run and the oil therein breaks down, it has been observed that $V_{OUT}$ increases over time as shown in FIG. 5.

Figure 6:
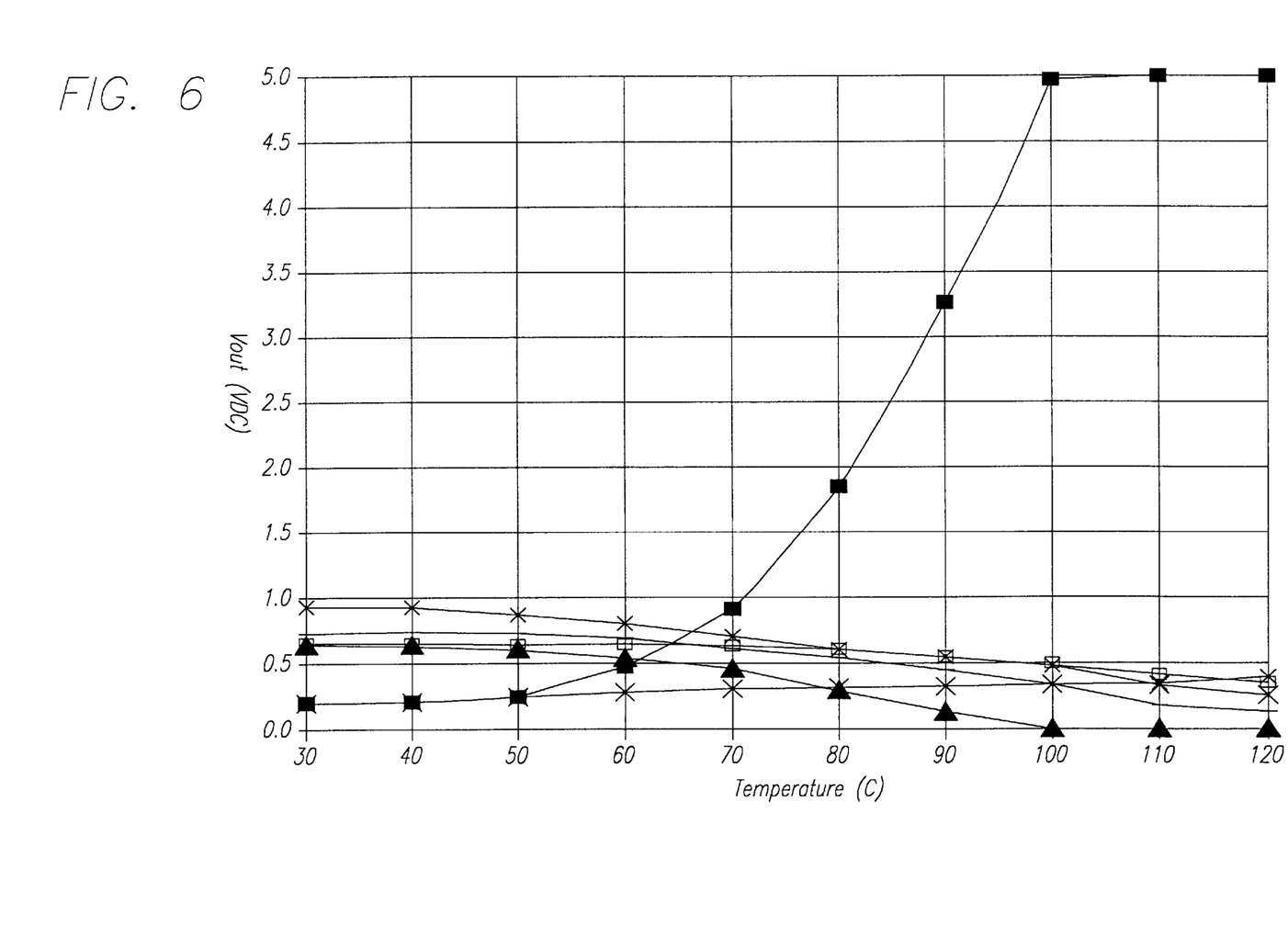
FIG. 6 is a plot of the output voltage (VDC) for various engine oil formulations over temperature (°C.)

FIG. 6 is a plot of $V_{OUT}$ for various engine oil formulations over engine oil temperature. The data points corresponding to each particular engine oil formulation are respectively represented by a different type of indicia. The following table shows which indicia correspond to each of the tested engine oil formulations.

| Brand | Indicia |
|-------|---------|
| A | ■ |
| B | □ |
| C | + |
| D | × |
| E | * |
| F | Δ |

$V_{OUT}$ for each of the tested formulations was observed to increase or decrease over temperature without the adjustment provided by the temperature sensitive resistor 52. As may be readily appreciated, the resistor 52 is particularly useful in accommodating most of the tested engine oil formulations where the temperature effects were observed to be substantially linear in nature. Brand B through F were well known nationally distributed brands of motor oil, while Brand A was a low quality brand. It is believed that one of the chemical additions in Brand A caused the unusual characteristic shown for plot A.

A key aspect of the present invention is that the electronics are adapted to employ the oil deterioration and level sensor capacitor ($C_\epsilon$) and the reference capacitor ($C_{ref}$) to generate both an oil deterioration output signal and an oil level output signal. Furthermore, the electronics are adapted to selectively provide the aforementioned signals to the electrical connector 26 and, in one preferred embodiment, to a single pair of output terminals. In order to achieve this dual functionality with the disclosed capacitor geometry, electronics such as those discussed below are employed.

FIG. 7 is a functional block diagram showing circuitry 700 for providing both an oil deterioration output signal and an oil level output signal. The majority of the circuitry 700 is preferably, but not necessarily, included within the hybrid 50.

Generally, the circuitry 700 is adapted to provide a meaningful output signal indicative of oil level, while also providing—when the gap is filled with oil—an output signal indicative of a degree of oil deterioration. Exemplary preferred circuitry 700 includes oil deterioration sensor output circuitry 200, oil level sensor output circuitry 200', switching circuits 702, 704 and a timer/trigger circuit 706 configured as shown in FIG. 7. An exemplary, preferred oil deterioration sensor output circuitry 200 is shown in FIG. 4 and has already been discussed. The oil level sensor output circuitry 200' is substantially identical to the circuitry 200. The only significant difference is that the external offset circuit 216 and external gain circuit 218 of circuitry 200' are adjusted to accommodate the more drastic changes in $C_\epsilon/C_L$ which result from changes in L. As appropriate, the circuitry 200' can also be modified to ensure an output signal of a single polarity.

The switching circuits 702, 704 and the timer/trigger circuit 706 are all conventional and operate, in conjunction with the circuitry 200 and the circuitry 200'. The switching circuit 702 receives an input signal from the timer 706. In response to this input signal, the switching circuit 702 provides the outputs of the sensing capacitor to circuitry 200 and circuitry 200'. The timer/trigger circuit 706 also provides an output signal to the switching circuit which, in turn, outputs $V_{OUT}$ and a tag signal. $V_{OUT}$ is one of $V_\epsilon$ and $V_L$ and is generated in a predetermined manner as controlled by the output of the timer/trigger circuit 706. The predetermined manner is preferably, but not necessarily, a periodic output $V_{OUT}$ which alternates between $V_\epsilon$ and $V_L$ with a 50% duty cycle. The frequency, duty cycle and amplitude of $V_{OUT}$ can be modified as desired.

Another key aspect of the present invention is that the disclosed capacitor geometry maximizes the area filled by the oil without significantly increasing the sensor package size. Furthermore, the cylindrical reference electrode 44 has been observed to partially compensate for the difference in dielectric constant of different oil brands and for any geometric changes caused by thermal expansion of the various materials comprising the sensor 20, as well as to cancel stray capacitance that arises in the wiring of the electrodes to the circuitry.

Another important benefit of the capacitor geometry of the present invention is the cost reduction that results from eliminating the gold plating of ceramic electrodes. The cylindrical electrodes can now be made out of aluminum with an anodized treatment to prevent shorts with the ground tube by oils with high metal particle content. A Teflon-based coating can also be used, with the additional benefit of discouraging soot adhesion to the surface of the electrodes. Finally, the gap between electrodes can now be increased while still obtaining large capacitance values since the area in contact with the oil is much larger. A preferred gap is 30 mils. Such a gap facilitates oil flow and ensures that all the oil will be renewed during oil change. The gap can be varied in response to the particular requirements of different sensor designs.

FIG. 3 shows an alternative preferred embodiment of the high-sensitivity capacitive oil deterioration and level sensor 20. The illustrated sensor 20 is substantially identical to the sensor of FIG. 1 except that the reference electrode 44 has been eliminated. Thus, $C_{ref} = C_{fixed}$. This alternative embodiment is appropriate for when the sensor 20 is to be used with a single type of oil and brand compensation is not required. This embodiment further reduces the number of components, thereby simplifying assembly and reducing cost. This also results in increased sensitivity to the changes in dielectric constant since there is no longer cancellation of $C_{ref}$ from $C_\epsilon$ as $\epsilon$ increases.

Figure 8:
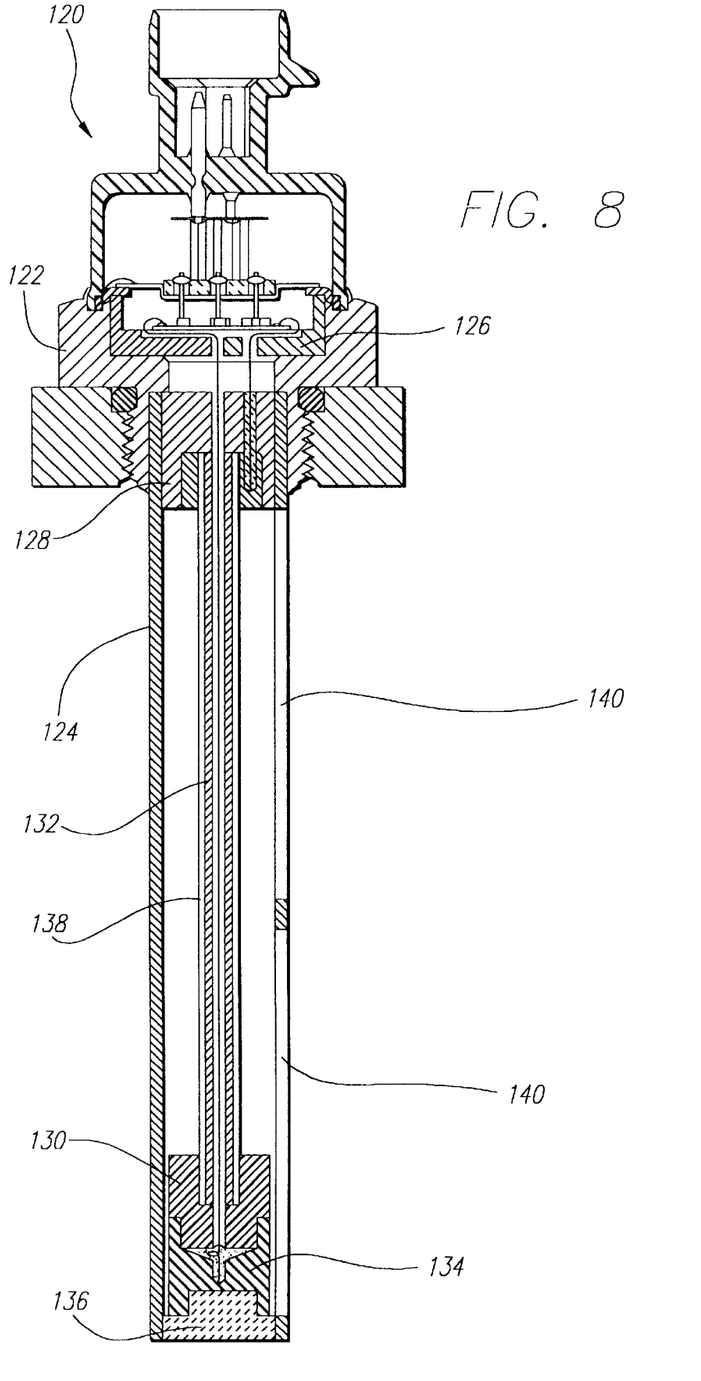
FIG. 8 is a cross-sectional side view of a second alternative exemplary preferred embodiment of a high-sensitivity capacitive oil deterioration and level sensor according to the present invention.

FIG. 8 shows another alternative preferred embodiment of the high-sensitivity capacitive oil deterioration and level sensor 120. As with the previously described embodiment, the sensor 120 includes a conductive surface which is employed as an electrode in a plurality of capacitors. The illustrated sensor 120 is the same as the sensor of FIG. 1 except as described below.

The sensor 120 includes a conductive housing member 122 and a conductive tube member 124 fitted within the housing member 122 as shown. The housing member 122 supports a top spacer 126 which is formed with apertures through which the wiring from the electrodes is routed to the hybrid assembly.

As shown in FIG. 8, a number of components are assembled within the tube member 124. Theses components include an upper spacer 128, lower spacer 130, conductive measuring tube 132, conductive electrode 134 and bottom cover 136. The measuring tube 132 is surrounded by a ceramic tube 138 and is fitted between the upper spacer 128 and the lower spacer 130 at opposing ends thereof. The conductive electrode 134, in turn, is fitted between the lower spacer 130 and the bottom cover 136. The lower spacer 130 preferably comprises an insulating plastic or hard rubber. An exemplary bottom cover 136 comprises a ceramic or plastic material.

The tube member 124 includes at least one longitudinal slot 140—two slots 140 are shown in FIG. 8—which permit oil to enter into the sensor 120. An exemplary preferred slot 140 spans from the bottom of the upper spacer 128 to the bottom cover 136 as shown. It should be appreciated that other slot configurations are additionally contemplated as being within the scope of the present invention.

In operation, the tube member 124 and the measuring tube 132 define a measuring electrode for oil level detection. The tube member 124 and the electrode 134 define a reference electrode for oil level detection. With regard to the oil deterioration sensing function, tube member 124 and the electrode 134 provide a measuring electrode for this function.

In conclusion, it is to be understood that the foregoing detailed description and the accompanying drawings illustrate the principles of the invention. However, various changes and modifications may be employed without departing from the spirit and scope of the invention. Accordingly, the present invention is not limited to the specific form shown in the drawings and described in detail hereinabove.

What is claimed is:

1. A high-sensitivity capacitive oil deterioration and level sensor comprising:
   a conductive housing member including a cylindrical portion with an inner surface defining a ground electrode, said housing member including a threaded outer surface adapted to be threaded into an oil container of an internal combustion engine, said housing member being formed with at least one port sized to allow oil within the oil container to enter into said cylindrical portion of said housing member;
   a conductive inner member including a cylindrical portion with an outer surface defining a measuring electrode, said inner member being secured within said housing member such that said ground electrode and said measuring electrode define an oil deterioration and level sensor capacitor;
   an electrical connector adapted to provide an electrical interface;
   a reference capacitor positioned within said housing member; and
   electronics positioned within said housing member, said electronics being electrically connected to said oil deterioration and level sensor capacitor, said reference capacitor, and said electrical connector, said electronics being adapted to generate an oil deterioration output signal and an oil level output signal employing said oil deterioration and level sensor capacitor and said reference capacitor and to provide said signals to said electrical connector.

2. The high-sensitivity capacitive oil deterioration and level sensor of claim 1 wherein:
   said electronics are adapted to selectively provide said signals to said electrical connector.

3. The high-sensitivity capacitive oil deterioration and level sensor of claim 2 wherein:
   said electronics are adapted to generate a tag signal.

4. The high-sensitivity capacitive oil deterioration and level sensor of claim 3 wherein:
   said electronics are adapted to provide said tag signal to said electrical connector.

5. The high-sensitivity capacitive oil deterioration and level sensor of claim 1 wherein:
   said electronics include:
      oil deterioration sensor output circuitry adapted to generate said oil deterioration output signal; and
      oil level sensor output circuitry adapted to generate said oil level output signal;
      said oil level sensor output circuitry having a gain different than said oil deterioration sensor output circuitry.

6. A high-sensitivity capacitive oil deterioration and level sensor comprising:
   a conductive housing member including a cylindrical portion with an inner surface defining a ground electrode, said housing member including a threaded outer surface adapted to be threaded into an oil container of an internal combustion engine, said housing member being formed with at least one port sized to allow oil within the oil container to enter into said cylindrical portion of said housing member;
   a conductive inner member including a cylindrical portion with an outer surface defining a measuring electrode, said inner member being sized to be fitted within said housing member such that said ground electrode and said measuring electrode define an oil deterioration and level sensor capacitor;
   an upper spacer positioned between said housing member and said inner member, said upper spacer being sized to maintain a substantially concentric relationship between said ground electrode and said measuring electrode; and
   electronics positioned within said housing member, said electronics being electrically connected to said oil deterioration and level sensor capacitor and adapted to provide an oil deterioration output signal and an oil level output signal employing said oil deterioration and level sensor capacitor.

7. The high-sensitivity capacitive oil deterioration and level sensor of claim 6 wherein:
   said electronics include a temperature variable element positioned within said housing and thermally connected with the oil.

8. The high-sensitivity capacitive oil deterioration and level sensor of claim 7 wherein:
   said inner member includes a channel formed within said cylindrical portion thereof; and
   said temperature variable element is positioned within said channel.

9. The high-sensitivity capacitive oil deterioration and level sensor of claim 6 wherein:
   said electronics include a hybrid circuit positioned within said housing member and supported by said upper spacer.

10. The high-sensitivity capacitive oil deterioration and level sensor of claim 6 further comprising:

a reference capacitor positioned within said housing member and electrically connected to said electronics;

said electronics being adapted to additionally employ said reference capacitor to provide said oil deterioration output signal and said oil level output signal.

11. The high-sensitivity capacitive oil deterioration and level sensor of claim 10 wherein:

said reference capacitor comprises a fixed reference capacitor.

12. The high-sensitivity capacitive oil deterioration and level sensor of claim 10 wherein:

said reference capacitor is formed by said ground electrode and a reference electrode positioned within said housing member.

13. The high-sensitivity capacitive oil deterioration and level sensor of claim 12 wherein:

said upper spacer is formed with a conduit through which an electrical connection between said electronics and said reference electrode is routed.

14. The high-sensitivity capacitive oil deterioration and level sensor of claim 12 further comprising:

a lower spacer positioned between said measuring electrode and said reference electrode.

15. A high-sensitivity capacitive oil deterioration and level sensor comprising:

a conductive housing member with an inner surface defining a ground electrode;

a conductive inner member with an outer surface defining a measuring electrode, said inner member being secured within said housing member such that a gap is maintained between said ground electrode and said measuring electrode, with said electrodes defining an oil deterioration and level sensor capacitor;

said housing member being attached to an oil container of an internal combustion engine and adapted to provide a fluidic connection between the oil container and said gap permitting oil within the oil container to flow into said gap; and electronics positioned within said housing member, said electronics being electrically connected to said oil deterioration and level sensor capacitor and adapted to employ said capacitor to generate signals indicative of a degree of deterioration and a level of the oil within said gap.

16. The high-sensitivity capacitive oil deterioration and level sensor of claim 15 wherein:

said signals include an oil deterioration output signal and an oil level output signal; and said electronics are adapted to generate said signals one at a time in a predetermined manner.

17. The high-sensitivity capacitive oil deterioration and level sensor of claim 15 further comprising:

a reference capacitor electrically connected to said electronics;

said electronics being adapted to additionally employ said reference capacitor to generate said signals.

18. The high-sensitivity capacitive oil deterioration and level sensor of claim 17 wherein:

said reference capacitor comprises:

an oil deterioration and level reference capacitor formed by said ground electrode and a reference electrode positioned within said housing member; and a fixed reference capacitor.

19. The high-sensitivity capacitive oil deterioration and level sensor of claim 15 further comprising:

a spacer positioned between said housing member and said inner member such that said measuring electrode is concentrically positioned relative to said ground electrode.

20. The high-sensitivity capacitive oil deterioration and level sensor of claim 19 wherein:

said ground electrode and said measuring electrode are cylindrically shaped.

21. A high-sensitivity capacitive oil deterioration and level sensor comprising:

a conductive tube member;

a conductive measuring tube secured within said tube member;

a conductive electrode secured within said tube member below said measuring tube;

said tube member and said measuring tube defining a measuring electrode for oil level detection;

said tube member and said electrode defining a reference electrode for oil level detection and a measuring electrode for oil deterioration sensing;

said tube member, said measuring tube and said electrode being electrically connected to electronics which are adapted to generate signals indicative of a degree of deterioration and a level of oil within the sensor.

22. A high-sensitivity capacitive oil deterioration and level sensor comprising:

at least three electrodes defining a plurality of capacitors which are electrically connected to electronics for generating signals indicative of a degree of deterioration and a level of oil within the sensor, one of said electrodes being employed as an electrode in at least two of said capacitors.

* * * * *